US011613206B2

(12) United States Patent
Lee et al.

(10) Patent No.: US 11,613,206 B2
(45) Date of Patent: Mar. 28, 2023

(54) INDOOR EMOTIONAL LIGHTING APPARATUS FOR IMPLEMENTING THREE-DIMENSIONAL PATTERN IN VEHICLE

(71) Applicants: HYUNDAI MOBIS Co., Ltd., Seoul (KR); NIFCO KOREA INC., Asan-si (KR)

(72) Inventors: Kwan Woo Lee, Yongin-si (KR); Jong Chae Lee, Asan-si (KR)

(73) Assignees: HYUNDAI MOBIS Co., Ltd., Seoul (KR); NIFCO KOREA INC., Asan-si (KR)

( * ) Notice: Subject to any disclaimer, the term of this patent is extended or adjusted under 35 U.S.C. 154(b) by 0 days.

(21) Appl. No.: 17/115,031

(22) Filed: Dec. 8, 2020

(65) Prior Publication Data

US 2021/0170944 A1 Jun. 10, 2021

(30) Foreign Application Priority Data

Dec. 9, 2019 (KR) .................. 10-2019-0163048

(51) Int. Cl.
| | |
|---|---|
| *B60Q 3/74* | (2017.01) |
| *F21V 5/02* | (2006.01) |
| *A61N 5/06* | (2006.01) |
| *B60Q 3/60* | (2017.01) |
| *F21V 5/00* | (2018.01) |
| *F21V 8/00* | (2006.01) |

(52) U.S. Cl.
CPC ........... *B60Q 3/745* (2017.02); *A61N 5/0618* (2013.01); *B60Q 3/60* (2017.02); *F21V 5/002* (2013.01); *F21V 5/004* (2013.01); *F21V 5/005* (2013.01); *F21V 5/007* (2013.01); *F21V 5/02* (2013.01); *G02B 6/005* (2013.01); *G02B 6/0036* (2013.01); *G02B 6/0038* (2013.01); *G02B 6/0053* (2013.01); *G02B 6/0055* (2013.01)

(58) Field of Classification Search
CPC .. G02B 6/0035; G02B 6/0036; G02B 6/0038; B60Q 3/62; B60Q 3/64
See application file for complete search history.

(56) References Cited

U.S. PATENT DOCUMENTS

| | | | |
|---|---|---|---|
| 10,670,865 B2 | 6/2020 | Song | |
| 2009/0190072 A1* | 7/2009 | Nagata | .................. G02B 6/005 362/601 |
| 2010/0309682 A1* | 12/2010 | Shiau | ................ G02F 1/133606 362/609 |

(Continued)

FOREIGN PATENT DOCUMENTS

| | | |
|---|---|---|
| DE | 20 2018 002 875 U1 | 8/2018 |
| KR | 10-1854746 B1 | 6/2018 |
| WO | WO-2021083800 A1 * | 5/2021 ............. F21V 11/14 |

*Primary Examiner* — Colin J Cattanach
(74) *Attorney, Agent, or Firm* — NSIP Law

(57) ABSTRACT

Provided herein is an indoor emotional lighting apparatus for implementing three-dimensional (3D) pattern for a vehicle, the indoor emotional lighting apparatus including a film portion on which a plurality of fine lenses each having a 3D pattern are arranged, a light source configured to emit light in a plurality of directions, and a light source guide portion configured to guide an optical path of the light source to allow the light emitted from the light source to be directed toward the film portion.

11 Claims, 10 Drawing Sheets

(56) References Cited

U.S. PATENT DOCUMENTS

| | | | |
|---|---|---|---|
| 2011/0227487 A1* | 9/2011 | Nichol | G02B 6/0018 |
| | | | 362/613 |
| 2011/0255303 A1* | 10/2011 | Nichol | G02B 6/0018 |
| | | | 362/606 |
| 2011/0273906 A1* | 11/2011 | Nichol | G02B 6/0028 |
| | | | 445/24 |
| 2015/0331169 A1* | 11/2015 | Jang | G02B 6/0023 |
| | | | 362/607 |
| 2015/0346499 A1* | 12/2015 | Minami | G02F 1/133605 |
| | | | 362/606 |
| 2018/0118101 A1* | 5/2018 | Salter | B60Q 3/20 |
| 2021/0284063 A1* | 9/2021 | Wang | B60Q 3/62 |
| 2022/0065425 A1* | 3/2022 | Cornelissen | F21V 11/14 |

\* cited by examiner

INDOOR EMOTIONAL LIGHTING APPARATUS FOR IMPLEMENTING THREE-DIMENSIONAL PATTERN IN VEHICLE

CROSS-REFERENCE TO RELATED APPLICATION

This application claims priority to and the benefit of Korean Patent Application No. 10-2019-0163048, filed on Dec. 9, 2019, the disclosure of which is incorporated herein by reference in its entirety.

BACKGROUND

1. Field of the Invention

The present invention relates to an indoor emotional lighting apparatus for a vehicle.

2. Discussion of Related Art

Recently, emotional lightings are widely applied to vehicle interiors. Typical emotional lighting employs an indirect lighting method in which light leaks through gaps between parts or a direct lighting method in which light passes through fine holes in an exterior.

Such emotional lightings stimulate emotions of users and positively affect physiological and cognitive aspects. In addition, the emotional lightings also have a function of aiding the users in improvement of their quality of life and satisfaction through optimal lighting experiences.

As described above, the current trend is that, by degrees, a function of lighting gradually includes an aesthetic and emotional function in addition to a function of simply illuminating light.

As part of the trend, recent indoor lighting apparatuses for vehicles are being developed in various ways so as to apply a next-generation slim cockpit design.

In particular, the indoor lighting apparatuses for vehicles are gradually developing through point, line, and surface shapes and moving away from the existing two-dimensional lightings, and currently, research and development on three-dimensional (3D) lightings is actively in progress in the relevant field.

SUMMARY OF THE INVENTION

The present invention is directed to solving the above problem and providing an indoor emotional lighting apparatus for implementing a three-dimensional pattern in a vehicle that is capable of providing an improved aesthetic feeling and improved three-dimensional (3D) lighting in a vehicle interior at a relatively low cost.

The problems to be solved by the present invention are not limited to those described above, and other problems not mentioned above should be clearly understood by those skilled in the art from the following description.

According to an aspect of the present invention, there is provided an indoor emotional lighting apparatus for a vehicle which includes a film portion on which a plurality of fine lenses each having a 3D pattern are arranged, a light source configured to emit light in a plurality of directions, and a light source guide portion configured to guide an optical path of the light source to allow the light emitted from the light source to be directed toward the film portion.

In this case, the light source guide portion may include a housing disposed below the film portion and having a predetermined air gap, an optical filter disposed on an upper end of the housing and configured to selectively transmit or reflect the light emitted from the light source, and an optic pattern member disposed in a partial section of a lower portion of the housing to emit the light reflected from the optical filter to the film portion.

The light source may be disposed on a lateral surface of the housing and may emit the light to each of the optical filter and the optic pattern member.

The light source may be disposed on the lateral surface of the housing, and a deflection angle of the light reflected from the optical filter may be determined according to a thickness of the housing.

The housing may have an air gap thickness which allows the deflection angle of the light reflected from the optical filter to be formed as an obtuse angle.

The optical filter may transmit only light having a wavelength in a predetermined band passing through the optic pattern member to the film portion.

The optical filter may include a light source hole provided on a path on which the light, which is emitted from the light source and passes through the optic pattern member, is directed toward the film portion.

The optical filter may reflect the light of the light source, which is emitted to a periphery of the light source hole, to the optic pattern member.

The indoor emotional lighting apparatus for a vehicle according to one embodiment may further include an exterior panel disposed to be spaced apart from the film portion and configured to cast the light, which passes through the film portion, to the vehicle interior.

Here, the exterior panel may be preferably formed of a material which gradationally transmits light from one side to the other side in a length direction.

According to another aspect of the present invention, there is provided an indoor emotional lighting apparatus for a vehicle which includes an exterior panel forming an exterior, light sources configured to emit light toward the exterior panel, and a film portion provided with a plurality of fine lenses disposed between the exterior panel and the light sources in a state of being spaced apart from each other, configured to transmit the light emitted from the light sources to the exterior panel, and having 3D patterns on a path to which the light is emitted.

The light source may preferably include a predetermined height difference with respect to the film portion so as to satisfy a light emission range and a sharpness condition.

The light source may be disposed at intervals in a transverse direction so as to satisfy a light emission range and a sharpness condition.

A design pattern portion including fine holes of various shapes, which are formed on the path of the light emitted from the light sources, may be bonded to upper ends of the light sources.

As a modified example unlike the above example, a design pattern portion including fine holes of various shapes, which are formed on the path of the light emitted from the light sources, may be disposed between the light sources and the film portion in a state of being spaced apart from the light sources and the film portion.

The film portion may preferably include an optical prism sheet having different 3D patterns.

The exterior panel may be formed such that a transparent material and a translucent material alternate in a length direction.

According to still another aspect of the present invention, there is provided an indoor emotional lighting apparatus for a vehicle which includes a light source configured to emit light toward an exterior panel, a design pattern portion including fine holes of various shapes through which the light emitted from the light source passes, and a film portion provided with fine lenses of different 3D patterns on a path of the light emitted from the light source and configured to adjust ascending and descending between the exterior panel and the design pattern portion.

The film portion may adjust a gap with respect to the light source according to a light emission range and a sharpness condition.

The light source may include a surface light source using an organic electro luminescence (EL) display.

In the design pattern portion, peripheries of the fine holes may be surface-treated with a non-transmissive material.

BRIEF DESCRIPTION OF THE DRAWINGS

The above and other objects, features and advantages of the present invention will become more apparent to those of ordinary skill in the art by describing exemplary embodiments thereof in detail with reference to the accompanying drawings, in which.

DETAILED DESCRIPTION OF EXEMPLARY EMBODIMENTS

Advantages and features of the present invention and methods of achieving them will be made clear from embodiments described in detail below with reference to the accompanying drawings. However, the present invention may be embodied in many different forms and should not be construed as being limited to the embodiments set forth herein. Rather, these embodiments are provided such that this disclosure will be thorough and complete and will fully convey the scope of the present invention to those of ordinary skill in the technical field to which the present invention pertains. The present invention is defined by the appended claims. Meanwhile, terms used herein are for the purpose of describing the embodiments and are not intended to limit the present invention. As used herein, the singular forms include the plural forms as well unless the context clearly indicates otherwise. The term "comprises" or "comprising" used herein does not preclude the presence or addition of one or more other elements, steps, operations, and/or devices other than stated elements, steps, operations, and/or devices.

Hereinafter, exemplary embodiments of the present invention will be described in detail with reference to the accompanying drawings.

Figure 1:
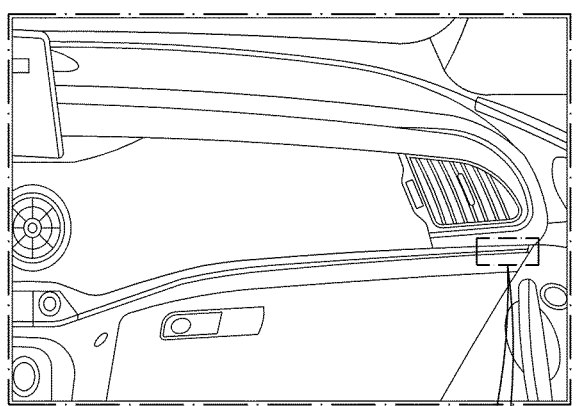
FIG. 1 is a diagram illustrating a state in which a three-dimensional (3D) lighting effect is applied through an indoor emotional lighting apparatus for a vehicle according to one embodiment of the present invention.
Figure 1:
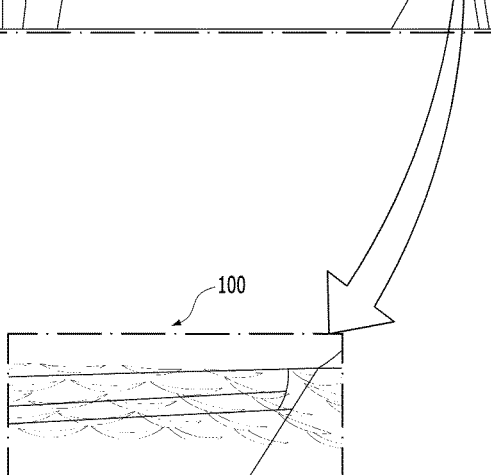

FIG. 1 is a diagram illustrating a state in which a three-dimensional (3D) lighting effect is applied through an indoor emotional lighting apparatus for a vehicle according to one embodiment of the present invention.

Referring to FIG. 1, an indoor emotional lighting device 100 for a vehicle may be installed in a vehicle interior to implement various (3D) patterns.

In the recent vehicle market, efforts are being made to slim down each structure in order to apply a next-generation slim cockpit design.

This is not just an effort to improve the design, but a part to reduce the unit cost of products and create a better environment. In line with this, patterns of lighting apparatuses which provide psychological stability of drivers in vehicle interiors are diversifying.

The indoor emotional lighting device 100 for a vehicle according to one embodiment of the present invention may implement a 3D pattern in which a sense of depth is felt, thereby deviating from the existing two-dimensional (2D) form.

This allows users (including drivers, passengers, and the like) to feel a sense of psychological stability as well as an aesthetic feeling to assist safe driving during vehicle traveling (especially, during night driving).

Figure 2:
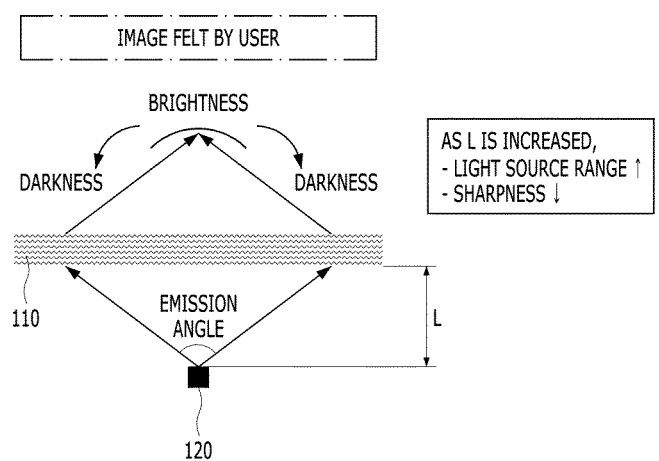
FIG. 2 is a diagram for describing concepts of a light source range and sharpness in the indoor emotional lighting apparatus for a vehicle according to one embodiment of the present invention.

FIG. 2 is a diagram for describing concepts of a light source range and sharpness in the indoor emotional lighting apparatus for a vehicle according to one embodiment of the present invention.

Referring to FIG. 2, light emitted from a light source 120 passes through a film portion 110 to be transmitted to a user as light of a 3D pattern.

Here, an image direction felt by the user corresponds to the vehicle interior, and the light source 120 is installed in a cockpit structure of the vehicle.

Generally, as a gap L between the light source 120 and the film portion 110 is increased, a light emission angle of the light source 120 is increased, and when light emitted from the light source 120 passes through the film portion 110, sharpness is decreased.

In other words, the gap L between the light source 120 and the film portion 110 is an important factor for determining a light source range and the sharpness. Therefore, configurations which can satisfy the light source range and the sharpness and relationship between the configurations are important.

In this case, the film portion 110 of the present invention is formed as lenticular lenses having different 3D patterns, and such a lenticular method employs a semi-cylindrical fine lens.

When numerous semi-cylindrical fine lenses are arranged in front of a display panel, images are differently refracted due to the semi-cylindrical fine lenses, and the refracted images enter both eyes of a user.

The use of a lens refracts light, and when pieces of light are made in parallel, a light-emitting diode (LED) is located at a focal point of the lens. When a target portion of lighting is located far from the lens, a target position of the lighting satisfies a condition similar to a condition of an image forming surface so that an image of the LED is visible.

Since such an afterimage causes non-uniformity of lighting, a major problem arises when lighting such as a medical headlight is used for closely observing a target.

As a method for solving the above problem, according to the present invention, a fine lens array having a small numerical aperture is employed behind a main lens from a light source.

Since light passing through the main lens meets the fine lens array and the light passing through each of the fine lenses spreads and mixed at a predetermined angle, an afterimage phenomenon at a target position of the lighting is reduced.

As described above, first to third embodiments of the present invention, which are capable of satisfying a light source range and sharpness and, simultaneously, implementing a 3D pattern will be described with reference to the accompanying drawings.

Figure 3:
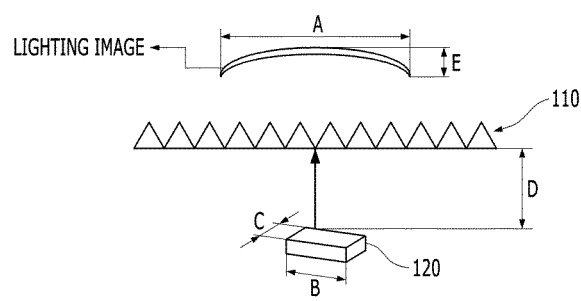
FIG. 3 is a diagram for describing setting of an influence factor of an optical prism sheet in the indoor emotional lighting apparatus for a vehicle according to one embodiment of the present invention.
Figure 4:
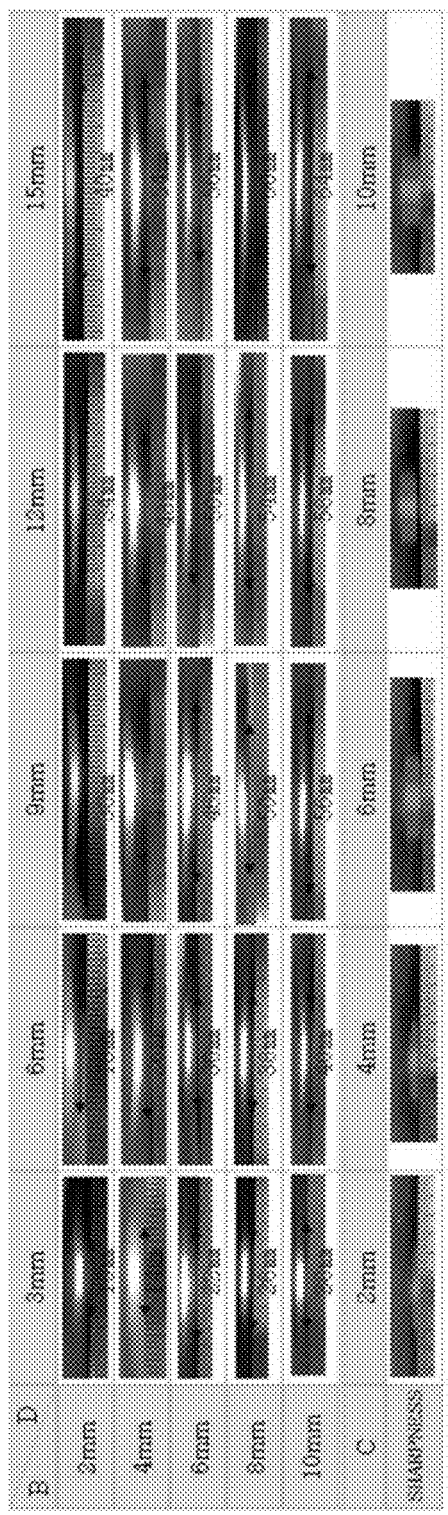
FIG. 4 is a diagram illustrating pattern images according to influence factors of the optical prism sheet shown in FIG. 3.

FIG. 3 is a diagram for describing setting of an influence factor of an optical prism sheet in the indoor emotional lighting apparatus for a vehicle according to one embodiment of the present invention, and FIG. 4 is a diagram illustrating pattern images according to influence factors of the optical prism sheet shown in FIG. 3.

Referring to FIGS. 3 and 4, the influence factors of the optical prism sheet (the film portion 110) include a 3D lighting pattern image length A, a transverse width B of the light source 120, a longitudinal width C of the light source 120, an air gap D, and a 3D pattern image depth E.

The 3D lighting pattern image length A means a left-right length of a 3D design image of the light source 120, which passes through the film portion 110.

The transverse width B of light source 120 means a transverse width of a lighting area which is projected onto the film portion 110.

The longitudinal width C of light source 120 means a longitudinal width of the lighting area which is projected onto the film portion 110.

The air gap D means a distance between the light source 120 and the film portion 110 and means a distance from an end portion of the lighting area projected onto the film portion 110 to the light source 120.

As can be confirmed in FIG. 4, when the transverse width B and the air gap D of the light source 120 are increased, the 3D lighting pattern image length A is increased. In this case, the longitudinal width C of the light source 120 does not significantly affect sharpness of the lighting.

First Embodiment

Figure 5:
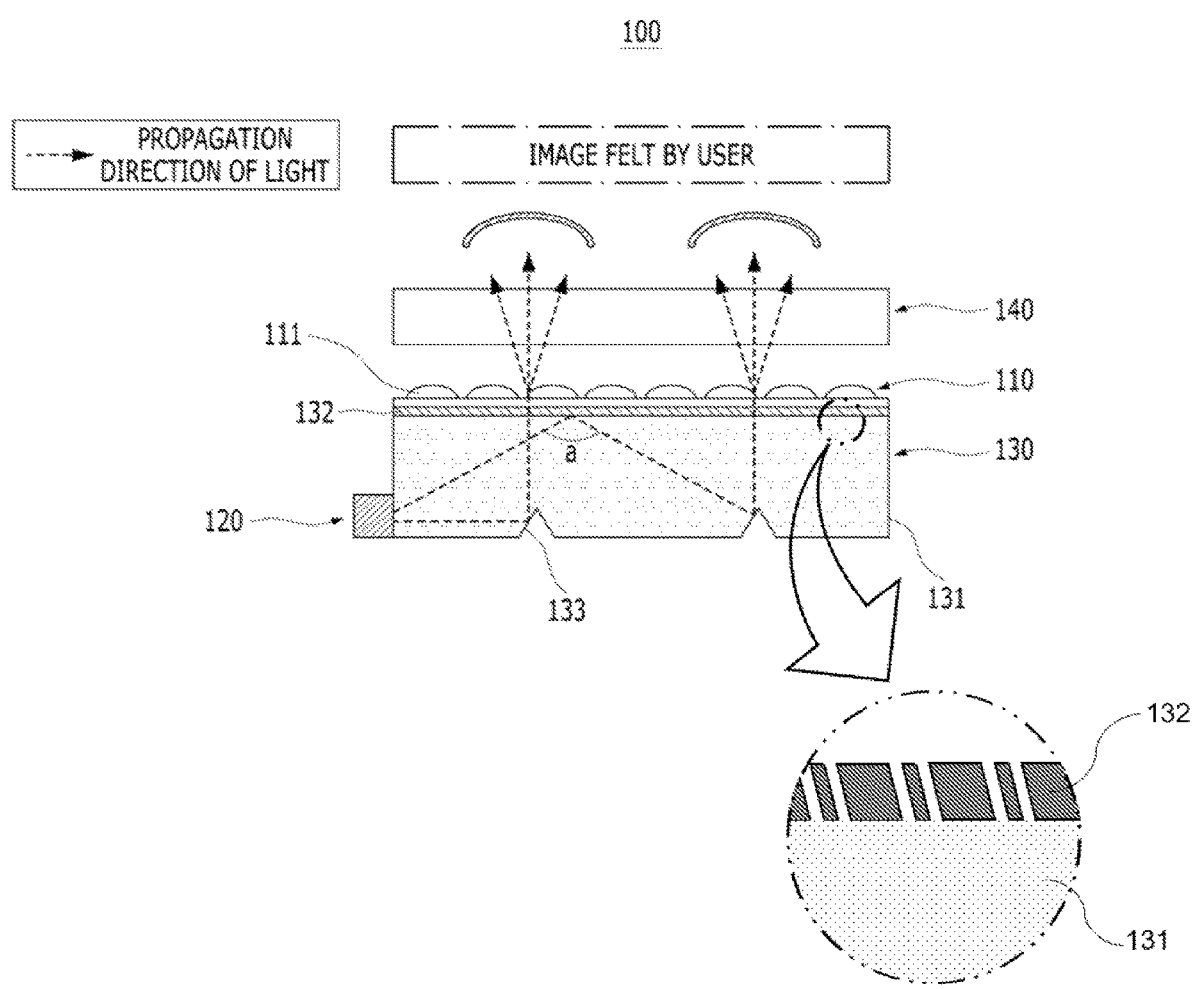
FIG. 5 is a schematic cross-sectional view illustrating an indoor emotional lighting apparatus for a vehicle according to a first embodiment of the present invention.

FIG. 5 is a schematic cross-sectional view illustrating an indoor emotional lighting apparatus for a vehicle according to a first embodiment of the present invention.

Referring to FIG. 5, an indoor emotional lighting device 100 for a vehicle includes a film portion 110, a light source 120, a light source guide portion 130, and an exterior panel 140.

The film portion 110 is formed in the form in which a plurality of fine lenses 111 each having a 3D pattern are arranged. A photosensitive emulsion is formed on a base surface of the film portion 110.

The light source 120 is formed as an LED which emits light in a plurality of directions.

The light source guide portion 130 guides an optical path of the light source 120 to allow light emitted from the light source 120 to be directed toward the film portion 110.

The light source guide portion 130 includes a housing 131, an optical filter 132, and optic pattern members 133.

The housing 131 is disposed below the film portion 110 and forms a body of the light source guide portion 130.

A thickness of the housing 131 serves as the air gap D shown in FIG. 3.

Here, the air gap means a distance between light sources, that is, a distance between the light source 120 and the film portion 110. When light is emitted from the light source 120, a deflection angle a should be secured so as to allow the light to be directed to the film portion 110.

The reason is that the light source 120 is disposed to emit light at a position on a lateral surface of the housing 131 of the light source guide portion 130.

In other words, the light source 120 is disposed on the lateral surface of the housing 131. In the light source 120, the deflection angle a of light reflected from the optical filter 132 is determined according to the thickness of the housing 131.

In this case, it is preferable that the housing 131 has an air gap thickness so as to allow the deflection angle a of the light reflected from the optical filter 132 to be formed as an obtuse angle.

When the deflection angle a of the light is formed as an acute angle, the thickness of the air gap is inevitably increased. This is also undesirable in terms of a manufacturing cost. Therefore, it is preferable that the deflection angle a of the light is formed as an obtuse angle.

The optical filter 132 is disposed on an upper end of the housing 131. The optical filter 132 has a function of selectively transmitting or reflecting light emitted from the light source 120.

To this end, the optical filter 132 may be formed in a structure having light source holes (not shown) which transmit only light having a wavelength in a predetermined band or transmit light only in a specific section.

In this case, in the structure in which the light source holes are formed in the optical filter 132, it is preferable that light emitted to peripheries of the light source holes is reflected instead of being transmitted.

The optic pattern members 133 are disposed in a partial section of a lower end of the housing 131. The optic pattern members 133 have inclined surfaces in the form of an angled shape. The inclined surfaces reflect the light emitted from the light source 120.

In this case, the light source 120 may simultaneously or sequentially emit light toward the optical filter 132 and the optic pattern members 133.

The optical filter 132 transmits only light, which has a wavelength in a predetermined band and passes through the optic pattern member 133, toward the film portion 110.

As another modified example, the light source holes of the optical filter 132 are located on a path on which light, which is emitted from the light source 120 and passes through the optic pattern members 133, is directed to the film portion 110.

Here, it is preferable that the optical filter 132 reflects light, which is emitted to the peripheries of the light source holes, to the optic pattern members 133.

The exterior panel 140 is disposed in a state of being spaced apart from the film portion 110. The exterior panel 140 casts light passing through the film portion 110 to the vehicle interior.

The exterior panel 140 may gradationally cast the light from one side to the other side in a length direction. That is, a surface of the exterior panel 140 may be formed of a material having a gradation effect.

The exterior panel 140 may be formed such that transparent and translucent materials alternate in the length direction. This may produce the form of lighting having various patterns.

Second Embodiment

Figure 6:
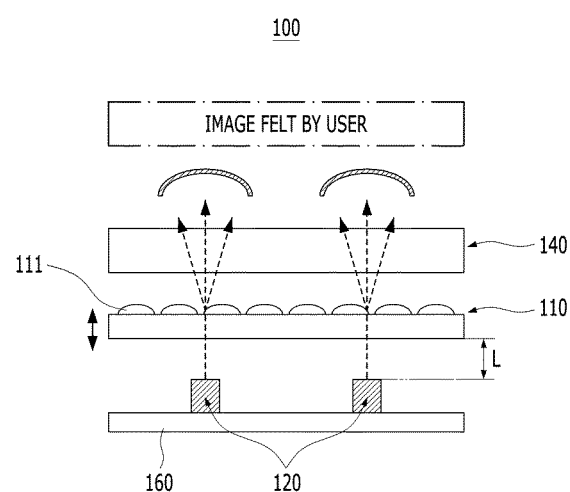
FIGS. 6 to 8 are schematic cross-sectional views illustrating an indoor emotional lighting apparatus for a vehicle according to a second embodiment of the present invention.
Figure 7:
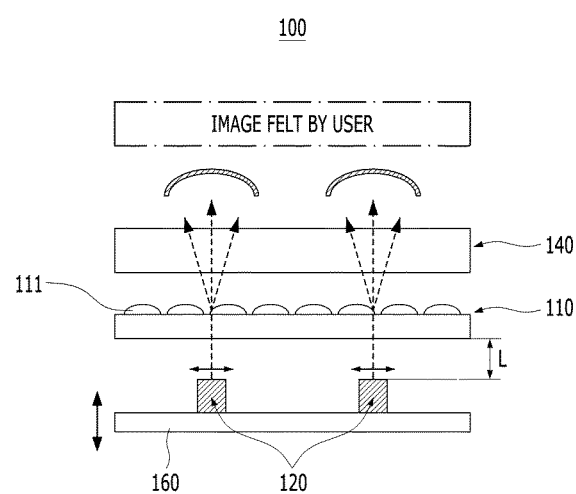
Figure 8:
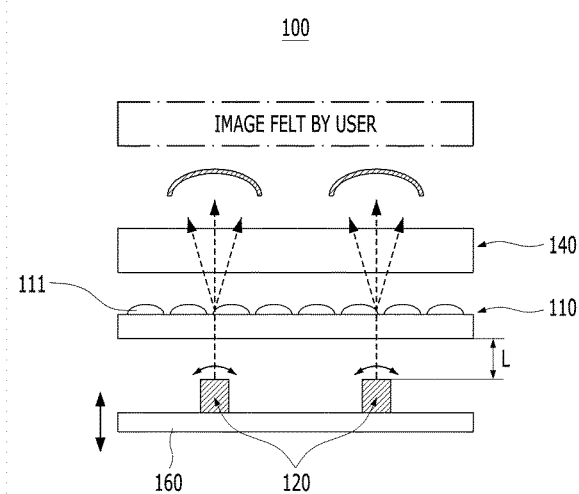

FIGS. 6 to 8 are schematic cross-sectional views illustrating an indoor emotional lighting apparatus for a vehicle according to a second embodiment of the present invention.

Referring to FIG. 6, an indoor emotional lighting device 100 for a vehicle includes light sources 120, a film portion 110, and an exterior panel 140.

In the second embodiment of the present invention, the light sources 120 are formed to be disposed below the film portion 110 to emit light without refraction of the light. That is, the light source 120 directly implements a design pattern through a point light source function.

In this case, since a gap L between the light source 120 and the film portion 110 is an important factor for determining a light source range and sharpness, when the gap L may be appropriately adjusted according to a situation, a 3D pattern may be implemented more effectively.

Thus, the film portion 110 may be formed in the form of being vertically adjusted to ascend or descend. In this case, the film portion 110 may be connected to a separate transfer device (not shown) and operated by a module which controls the separate transfer device.

Meanwhile, it is preferable that the light source 120 has a predetermined height difference (an interval L) with respect to the film portion 110 so as to satisfy a light emission range (the light source range) and a sharpness condition. Here, the predetermined height difference means an optimal height difference satisfying the light source range and the sharpness condition and may be appropriately varied according to shapes and structures of the light source 120 and the film portion 110.

According to a basic form of the present invention, the light sources 120 are disposed at intervals in the transverse direction to satisfy the light source range and the sharpness condition.

However, according to a change condition of the above light source range and the above sharpness, the light sources 120 may be disposed at different heights.

An indoor emotional lighting device 100 for a vehicle in FIG. 7 is a modified example which is different from that of FIG. 6 and is formed in a structure in which the film portion 110 has a fixed form and a holder 160 holding the light sources 120 is vertically adjusted to ascend or descend.

Here, the holder 160 connects the light sources 120 to be slidably moved in the transverse direction.

An indoor emotional lighting device 100 for a vehicle in FIG. 8 is a modified example of FIG. 5 and has the same structure in which the holder 160 is vertically adjusted to ascend or descend but differs in that emission angles of the light sources 120 are varied.

That is, the light sources 120 in FIG. 8 may be hinge-connected to the holder 160 to be formed in a structure capable of being pivoted in a left-right direction.

In this case, the light sources 120 may emit light toward the film portion 110 at various angles to allow the user to feel lighting of a larger variety of 3D patterns.

Third Embodiment

Figure 9:
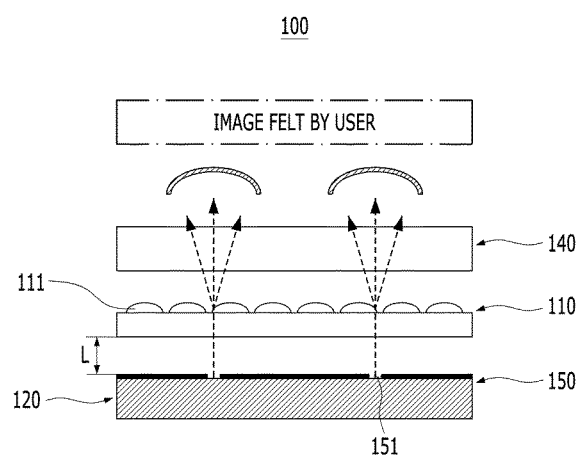
FIGS. 9 and 10 are schematic cross-sectional views illustrating an indoor emotional lighting apparatus for a vehicle according to a third embodiment of the present invention.
Figure 10:
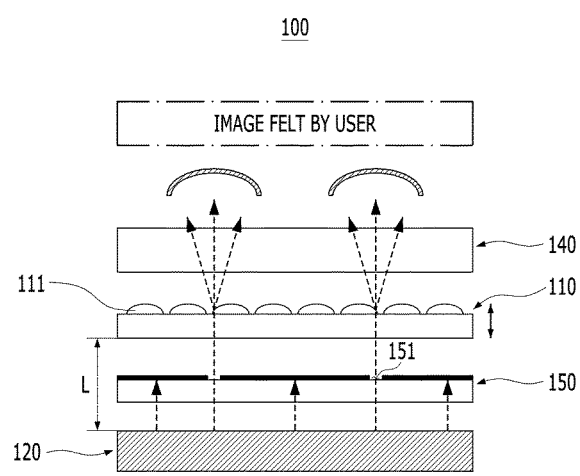

FIGS. 9 and 10 are schematic cross-sectional views illustrating an indoor emotional lighting apparatus for a vehicle according to a third embodiment of the present invention.

Referring to FIGS. 9 and 10, an indoor emotional lighting device 100 for a vehicle includes a light source 120, a design pattern portion 150, and a film portion 110.

The light source 120 emits light to an exterior panel 140.

The design pattern portion 150 has various shaped fine holes 151 through which the light emitted from the light source 120 passes. Here, the fine holes 151 may be formed in various geometric shapes such as circular shapes, triangular shapes, quadrangular shapes, pentagonal shapes, and hexagonal shapes.

In the design pattern portion 150, peripheries of the fine holes 151 may be surface-treated with a non-transmissive material.

The design pattern portion 150 may be disposed in a state of being bonded to or spaced apart from the light source 120.

Here, an upper surface of the light source 120 implemented in the form of a surface light source may be bonded to the design pattern portion 150 through masking coating, taping, or the like.

The film portion 110 is provided with fine lenses 111 having different 3D patterns on a path of the light emitted from the light source 120 and is adjusted to ascend or descend between the exterior panel 140 and the design pattern portion 150.

A gap between the film portion 110 and the light source 120 may be adjusted according to a light source range and a sharpness condition of the light source 120.

In this case, the light source 120 may be formed as a surface light source using an organic electro luminescence (EL) display.

Light emitted from the light source 120 reaches the film portion 110 through the fine holes 151 of the design pattern portion 150, and the light reaching the film portion 110 is deflected to pass through the exterior panel 140, which is treated with a transparent or translucent material, thereby being transmitted to the user.

In this case, the user may feel a sense of depth without distortion of the lighting implemented in the 3D pattern.

In accordance with the present invention, a gap between a light source and a film portion is adjusted so that a light source range can be increased and, simultaneously, a 3D pattern can be implemented with optimal sharpness.

In particular, in accordance with the present invention, a 3D pattern in which a sense of depth is felt can be implemented away from the existing 2D form.

Therefore, the present invention allows users (including drivers, passengers, and the like) to feel a sense of psychological stability as well as an aesthetic feeling and can assist safe driving during vehicle traveling (especially, during night driving).

The present invention is not limited to the above-described embodiments, and various modifications may be made without departing from the spirit of the present invention.

What is claimed is:
1. A lighting apparatus for implementing three-dimensional (3D) pattern, the lighting apparatus comprising:
a film portion on which a lenticular lens array having a plurality of 3D patterns is arranged, the lenticular lens array includes a plurality of semi-cylindrical lenses;

a light source configured to emit light in a plurality of directions; and a light source guide portion configured to guide an optical path of the light source to allow the light emitted from the light source to be directed toward the film portion, wherein the light source guide portion includes:

a housing disposed below the film portion and having a predetermined thickness;

an optical filter disposed on an upper end of the housing and configured to selectively transmit or reflect the light emitted from the light source; and an optic pattern member disposed in a partial section of a lower portion of the housing to reflect light emitted from the light source including light reflected from the optical filter to the optic pattern member.

2. The lighting apparatus of claim 1, wherein the light source is disposed on a lateral surface of the housing and emits the light to each of the optical filter and the optic pattern member.

3. The lighting apparatus of claim 1, wherein the light source is disposed on a lateral surface of the housing, and a deflection angle of the light reflected from the optical filter is determined according to a thickness of the housing.

4. The lighting apparatus of claim 3, wherein the thickness of the housing allows the deflection angle of the light reflected from the optical filter to be formed as an obtuse angle.

5. The lighting apparatus of claim 1, wherein the optical filter transmits only light having a wavelength in a predetermined band passing through the optic pattern member to the film portion.

6. The lighting apparatus of claim 1, wherein the optical filter includes a light source hole provided on a path on which the light, which is emitted from the light source and reflected through the optic pattern member, is directed toward the film portion.

7. The lighting apparatus of claim 6, wherein the optical filter reflects the light of the light source, which is emitted to a periphery of the light source hole, to the optic pattern member.

8. The lighting apparatus of claim 1, further comprising an exterior panel disposed to be spaced apart from the film portion and configured to cast the light, which passes through the film portion, to the vehicle interior.

9. The lighting apparatus of claim 8, wherein the exterior panel is formed of a material which gradationally transmits light from one side to the other side in a length direction.

10. The lighting apparatus of claim 1, wherein the plurality of semi-cylindrical lenses each having a respective 3D pattern.

11. The lighting apparatus of claim 1, wherein the optic pattern member includes a side having an incline angle relative to a plane defined by the optical filter.

* * * * *